US012343547B2

(12) United States Patent
Lopez

(10) Patent No.: US 12,343,547 B2
(45) Date of Patent: Jul. 1, 2025

(54) CONNECTORS FOR AN ELECTRICAL STIMULATION SYSTEM AND METHODS OF MAKING AND USING

(71) Applicant: Boston Scientific Neuromodulation Corporation, Valencia, CA (US)

(72) Inventor: Thomas Paul Lopez, Sunland, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 311 days.

(21) Appl. No.: 17/888,736

(22) Filed: Aug. 16, 2022

(65) Prior Publication Data

US 2023/0056675 A1 Feb. 23, 2023

Related U.S. Application Data

(60) Provisional application No. 63/234,884, filed on Aug. 19, 2021.

(51) Int. Cl.
*A61N 1/375* (2006.01)
*A61N 1/08* (2006.01)
*B23K 1/00* (2006.01)

(52) U.S. Cl.
CPC .............. *A61N 1/3752* (2013.01); *A61N 1/08* (2013.01); *B23K 1/0016* (2013.01)

(58) Field of Classification Search
CPC ....... A61N 1/3752; A61N 1/08; B23K 1/0016
USPC .......................................................... 439/12
See application file for complete search history.

(56) References Cited

U.S. PATENT DOCUMENTS

| | | | |
|---|---|---|---|
| 3,222,471 A | 12/1965 | Steinkamp | |
| 3,601,747 A | 8/1971 | Prall et al. | |
| 3,718,142 A | 2/1973 | Mulier | |
| 3,757,789 A | 9/1973 | Shanker | |
| 3,771,106 A | 11/1973 | Matsumoto et al. | |
| 3,908,668 A | 9/1975 | Bolduc | |
| 3,951,154 A | 4/1976 | Hartlaub | |
| 3,990,727 A | 11/1976 | Gallagher | |
| 4,003,616 A | 1/1977 | Springer | |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

"Structure and Properties of Ceramics, 2018, The American Ceramic Society" (Year: 2018).

(Continued)

*Primary Examiner* — Peter G Leigh
(74) *Attorney, Agent, or Firm* — Branch Partners PLLC; Bruce E. Black

(57) ABSTRACT

A connector that includes contact assemblies and non-conductive stack spacers separating the contact assemblies from each other, the contact assemblies and the stack spacers defining a connector lumen configured to receive a portion of an electrical stimulation lead. The contact assemblies and stack spacers are brazed together forming a sealed connector stack that resists passage of fluid between the contact assemblies and stack spacers. Alternatively or additionally, the stack spacers are made of a non-conductive ceramic, crystalline, or glass material.

20 Claims, 6 Drawing Sheets

(56) References Cited

U.S. PATENT DOCUMENTS

| | | |
|---|---|---|
| 4,072,154 A | 2/1978 | Anderson et al. |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,262,673 A | 4/1981 | Kinney et al. |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,934,366 A | 6/1990 | Truex et al. |
| 4,942,876 A | 7/1990 | Gotthardt |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,069,209 A | 12/1991 | Posin |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,957,968 A | 9/1999 | Belden et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,029,089 A | 2/2000 | Hawkins et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,269,266 B1 | 7/2001 | Leysieffer |
| 6,271,094 B1 | 8/2001 | Boyd et al. |
| 6,295,944 B1 | 10/2001 | Lovett |
| 6,305,962 B1 | 10/2001 | Maher |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B1 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,575,759 B1 | 6/2003 | Ollivier |
| 6,604,283 B1 | 8/2003 | Kuzma |
| 6,605,094 B1 | 8/2003 | Mann et al. |
| 6,609,029 B1 | 8/2003 | Mann et al. |

(56) References Cited

U.S. PATENT DOCUMENTS

| | | |
|---|---|---|
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,687,538 B1 | 2/2004 | Hrdlicka et al. |
| 6,705,900 B2 | 3/2004 | Sommer et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,895,280 B2 | 5/2005 | Meadows et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooj et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,819 B1 | 9/2006 | O'Hara |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,654,843 B2 | 2/2010 | Olson et al. |
| 7,668,601 B2 | 2/2010 | Hegland et al. |
| 7,672,734 B2 | 3/2010 | Anderson et al. |
| 7,711,427 B2 * | 5/2010 | Janzig ............ A61N 1/3752 607/38 |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 * | 10/2010 | Rey ............ H01R 13/5224 607/37 |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,890,175 B1 * | 2/2011 | Rey ............ H01R 13/5224 607/37 |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,095,217 B2 * | 1/2012 | Ruschel ............ A61N 1/3752 607/38 |
| 8,099,177 B2 | 1/2012 | Dahlberg |
| 8,100,726 B2 | 1/2012 | Harlan et al. |
| 8,131,370 B2 * | 3/2012 | Janzig ............ H01R 43/20 607/37 |
| 8,140,163 B1 | 3/2012 | Daglow et al. |
| 8,140,172 B1 | 3/2012 | Jones et al. |
| 8,162,684 B1 | 4/2012 | Sochor |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,267,708 B1 | 9/2012 | Sochor |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,268 B2 * | 1/2013 | Phillips ............ A61N 1/3752 607/27 |
| 8,364,278 B2 | 1/2013 | Pianca et al. |
| 8,369,951 B2 * | 2/2013 | Smith ............ A61N 1/3752 607/37 |
| 8,391,985 B2 | 3/2013 | McDonald |
| 8,412,330 B2 | 4/2013 | Kast et al. |
| 8,473,061 B2 | 6/2013 | Moffitt et al. |
| 8,527,054 B2 | 9/2013 | North |
| 8,543,222 B1 | 9/2013 | Sochor |
| 8,548,582 B2 * | 10/2013 | McDonald ............ A61N 1/3718 607/2 |
| 8,571,665 B2 | 10/2013 | Moffitt et al. |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,738,138 B2 | 5/2014 | Funderburk et al. |
| 8,738,141 B2 * | 5/2014 | Smith ............ A61N 1/3752 607/46 |
| 8,751,002 B2 | 6/2014 | Kast et al. |
| 8,761,887 B2 | 6/2014 | Schramm et al. |
| 8,784,143 B2 | 7/2014 | Edgell et al. |
| 8,792,993 B2 | 7/2014 | Pianca et al. |
| 8,831,742 B2 * | 9/2014 | Pianca ............ H01R 43/16 607/116 |
| 8,849,396 B2 | 9/2014 | DeRohan et al. |
| 8,849,415 B2 | 9/2014 | Bedenbaugh |
| 8,897,876 B2 * | 11/2014 | Sundaramurthy ... A61N 1/3752 607/38 |
| 8,897,891 B2 | 11/2014 | Romero |

(56) References Cited

U.S. PATENT DOCUMENTS

| | | | |
|---|---|---|---|
| 8,968,331 B1* | 3/2015 | Sochor | A61B 17/3468 |
| | | | 606/129 |
| 9,101,775 B2* | 8/2015 | Barker | A61N 1/3752 |
| 9,138,586 B2* | 9/2015 | Eiger | A61N 1/3752 |
| 9,149,630 B2 | 10/2015 | Howard et al. | |
| 9,162,048 B2 | 10/2015 | Romero et al. | |
| 9,162,055 B2 | 10/2015 | Pianca et al. | |
| 9,168,376 B2* | 10/2015 | Janzig | A61N 1/3752 |
| 9,225,114 B2 | 12/2015 | Sinclair | |
| 9,234,591 B2 | 1/2016 | Dilmaghanian et al. | |
| 9,270,070 B2* | 2/2016 | Pianca | A61N 1/0534 |
| 9,283,396 B2* | 3/2016 | Janzig | A61N 1/3752 |
| 9,289,596 B2 | 3/2016 | Leven | |
| 9,302,094 B2 | 4/2016 | Govea | |
| 9,352,147 B2 | 5/2016 | Nguyen-stella et al. | |
| 9,381,348 B2 | 7/2016 | Romero et al. | |
| 9,403,022 B2* | 8/2016 | Ries | A61N 1/37518 |
| 9,409,032 B2 | 8/2016 | Brase et al. | |
| 9,440,066 B2 | 9/2016 | Black | |
| 9,482,666 B2 | 11/2016 | Domenyuk et al. | |
| 9,492,666 B2 | 11/2016 | Smith et al. | |
| 9,498,618 B2 | 11/2016 | Stetson et al. | |
| 9,498,620 B2* | 11/2016 | Romero | H01R 43/26 |
| 9,504,839 B2 | 11/2016 | Leven | |
| 9,555,242 B2 | 1/2017 | Hartley et al. | |
| 9,564,749 B2 | 2/2017 | Boutaud | |
| 9,604,068 B2 | 3/2017 | Malinowski | |
| 9,656,093 B2* | 5/2017 | Villarta | A61N 1/05 |
| 9,662,506 B2 | 5/2017 | Govea | |
| 9,770,598 B2* | 9/2017 | Malinowski | H01R 13/187 |
| 9,775,988 B2 | 10/2017 | Govea et al. | |
| 9,782,582 B2 | 10/2017 | Govea et al. | |
| 9,839,787 B2 | 12/2017 | Villarta et al. | |
| 9,855,413 B2* | 1/2018 | Vadlamudi | A61N 1/05 |
| 9,865,533 B2 | 1/2018 | Ruben et al. | |
| 9,878,148 B2 | 1/2018 | Leven et al. | |
| 9,931,513 B2* | 4/2018 | Kelsch | A61N 1/04 |
| 10,071,253 B2* | 9/2018 | Janzig | A61N 1/3752 |
| 10,342,983 B2 | 7/2019 | Nagei et al. | |
| 10,363,424 B2* | 7/2019 | Janzig | A61N 1/3752 |
| 10,535,945 B2 | 1/2020 | Dilmaghanian et al. | |
| 11,045,656 B2 | 6/2021 | Nageri et al. | |
| 2001/0023368 A1 | 9/2001 | Black et al. | |
| 2002/0095079 A1 | 7/2002 | Putz | |
| 2002/0128692 A1 | 9/2002 | Imani et al. | |
| 2002/0143376 A1 | 10/2002 | Chinn et al. | |
| 2002/0156513 A1 | 10/2002 | Borkan | |
| 2002/0183817 A1 | 12/2002 | Van Venrooij et al. | |
| 2003/0050672 A1 | 3/2003 | Dahlberg | |
| 2003/0073348 A1 | 4/2003 | Ries et al. | |
| 2003/0163171 A1 | 8/2003 | Kast et al. | |
| 2004/0064164 A1 | 4/2004 | Ries et al. | |
| 2004/0176816 A1 | 9/2004 | Singhal et al. | |
| 2004/0230268 A1 | 11/2004 | Huff et al. | |
| 2004/0260373 A1 | 12/2004 | Ries et al. | |
| 2004/0267332 A1 | 12/2004 | Kast et al. | |
| 2005/0015130 A1 | 1/2005 | Gill | |
| 2005/0027326 A1 | 2/2005 | Ries et al. | |
| 2005/0027327 A1 | 2/2005 | Ries et al. | |
| 2005/0038489 A1 | 2/2005 | Grill | |
| 2005/0043770 A1 | 2/2005 | Hine et al. | |
| 2005/0043771 A1 | 2/2005 | Sommer et al. | |
| 2005/0055062 A1 | 3/2005 | Correas et al. | |
| 2005/0113886 A1 | 5/2005 | Fischell et al. | |
| 2005/0137665 A1 | 6/2005 | Cole | |
| 2005/0171587 A1 | 8/2005 | Daglow et al. | |
| 2005/0186829 A1 | 8/2005 | Balsells | |
| 2005/0234521 A1 | 10/2005 | Balsells | |
| 2005/0272280 A1 | 12/2005 | Osypka | |
| 2006/0015163 A1 | 1/2006 | Brown | |
| 2006/0025841 A1 | 2/2006 | McIntyre | |
| 2006/0030918 A1 | 2/2006 | Chinn | |
| 2006/0089681 A1 | 4/2006 | Tumlinson et al. | |
| 2006/0167522 A1 | 7/2006 | Malinowski | |
| 2006/0224208 A1 | 10/2006 | Naviaux | |
| 2006/0247697 A1 | 11/2006 | Sharma et al. | |
| 2006/0247749 A1 | 11/2006 | Colvin | |
| 2006/0259106 A1 | 11/2006 | Arnholdt et al. | |
| 2007/0042648 A1 | 2/2007 | Balsells | |
| 2007/0142889 A1 | 6/2007 | Whitehurst et al. | |
| 2007/0150036 A1 | 6/2007 | Anderson | |
| 2007/0161294 A1 | 7/2007 | Brase et al. | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2007/0225772 A1 | 9/2007 | Lahti et al. | |
| 2008/0009192 A1 | 1/2008 | Kast et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0139031 A1 | 6/2008 | Ries et al. | |
| 2008/0177167 A1 | 7/2008 | Janzig et al. | |
| 2008/0198530 A1 | 8/2008 | Zhao et al. | |
| 2008/0208277 A1 | 8/2008 | Janzig et al. | |
| 2008/0208278 A1 | 8/2008 | Janzig et al. | |
| 2008/0208279 A1 | 8/2008 | Janzig et al. | |
| 2008/0215125 A1 | 9/2008 | Farah et al. | |
| 2008/0255647 A1 | 10/2008 | Jensen et al. | |
| 2008/0274651 A1 | 11/2008 | Boyd et al. | |
| 2009/0012591 A1 | 1/2009 | Barker | |
| 2009/0054941 A1 | 2/2009 | Eggen et al. | |
| 2009/0054949 A1 | 2/2009 | Alexander et al. | |
| 2009/0187222 A1 | 7/2009 | Barker | |
| 2009/0204192 A1 | 8/2009 | Carlton et al. | |
| 2009/0233491 A1 | 9/2009 | Barker et al. | |
| 2009/0264943 A1 | 10/2009 | Barker | |
| 2009/0270940 A1 | 10/2009 | Deininger et al. | |
| 2009/0270961 A1* | 10/2009 | Ruschel | A61N 1/3752 |
| | | | 439/660 |
| 2009/0276021 A1 | 11/2009 | Meadows et al. | |
| 2009/0287191 A1 | 11/2009 | Ferren et al. | |
| 2010/0029127 A1 | 2/2010 | Sjostedt | |
| 2010/0030298 A1 | 2/2010 | Martens et al. | |
| 2010/0036468 A1 | 2/2010 | Decre et al. | |
| 2010/0042169 A1 | 2/2010 | Barker | |
| 2010/0057176 A1 | 3/2010 | Barker | |
| 2010/0070009 A1 | 3/2010 | Barker | |
| 2010/0070012 A1 | 3/2010 | Chinn et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |
| 2010/0094387 A1 | 4/2010 | Pianca et al. | |
| 2010/0100152 A1 | 4/2010 | Martens et al. | |
| 2010/0114210 A1 | 5/2010 | Donofrio et al. | |
| 2010/0114249 A1 | 5/2010 | Wahlstrand et al. | |
| 2010/0268298 A1 | 10/2010 | Moffitt et al. | |
| 2010/0269338 A1 | 10/2010 | Dye | |
| 2010/0269339 A1 | 10/2010 | Dye et al. | |
| 2010/0287770 A1 | 11/2010 | Dadd et al. | |
| 2011/0004267 A1 | 1/2011 | Meadows | |
| 2011/0005069 A1 | 1/2011 | Pianca | |
| 2011/0005829 A1 | 1/2011 | Pianca et al. | |
| 2011/0022100 A1 | 1/2011 | Brase et al. | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0184479 A1 | 7/2011 | Kast et al. | |
| 2011/0184480 A1 | 7/2011 | Kast et al. | |
| 2011/0238129 A1 | 9/2011 | Moffitt et al. | |
| 2011/0245903 A1 | 10/2011 | Schulte et al. | |
| 2011/0270330 A1 | 11/2011 | Janzig et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0035692 A1 | 2/2012 | Cantlon et al. | |
| 2012/0046710 A1 | 2/2012 | DiGiore et al. | |
| 2012/0053646 A1 | 3/2012 | Brase et al. | |
| 2012/0071937 A1 | 3/2012 | Sundaramurthy et al. | |

(56) References Cited

U.S. PATENT DOCUMENTS

| | | |
|---|---|---|
| 2012/0071949 A1 | 3/2012 | Pianca et al. |
| 2012/0100729 A1 | 4/2012 | Edidin et al. |
| 2012/0165911 A1 | 6/2012 | Pianca |
| 2012/0167385 A1 | 7/2012 | McGiboney et al. |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0277760 A1 | 11/2012 | Kratoska et al. |
| 2012/0316615 A1 | 12/2012 | DiGiore et al. |
| 2013/0035732 A1 | 2/2013 | Miltich et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0094674 A1 | 4/2014 | Nurmikko et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0213118 A1 | 7/2014 | Glynn et al. |
| 2014/0214130 A1 | 7/2014 | Lopez et al. |
| 2014/0277260 A1 | 9/2014 | Khalil et al. |
| 2014/0350655 A1 | 11/2014 | North et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0018916 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0051681 A1 | 2/2015 | Hershey |
| 2015/0066120 A1 | 3/2015 | Govea |
| 2015/0119965 A1 | 4/2015 | Govea |
| 2015/0127063 A1 | 5/2015 | Datta |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0022984 A1 | 1/2016 | Oster et al. |
| 2016/0059019 A1 | 3/2016 | Malinowski et al. |
| 2016/0082254 A1 | 3/2016 | Moffitt et al. |
| 2016/0082255 A1 | 3/2016 | Moffitt et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0220826 A1 | 8/2016 | Funderburk |
| 2016/0228692 A1 | 8/2016 | Steinke et al. |
| 2016/0250466 A1 | 9/2016 | Boggs, II et al. |
| 2016/0263384 A1 | 9/2016 | Stevenson et al. |
| 2016/0296745 A1 | 10/2016 | Govea et al. |
| 2016/0375238 A1 | 12/2016 | Leven et al. |
| 2017/0014635 A1 | 1/2017 | Villarta et al. |
| 2017/0056652 A1 | 3/2017 | Gittard et al. |
| 2017/0072187 A1 | 3/2017 | Howard et al. |
| 2017/0143978 A1 | 5/2017 | Barker |
| 2017/0151438 A1 | 6/2017 | Orinski |
| 2017/0151440 A1 | 6/2017 | Parramon et al. |
| 2017/0203104 A1 | 7/2017 | Nageri et al. |
| 2017/0216604 A1 | 8/2017 | Villarta et al. |
| 2017/0232264 A1 | 8/2017 | Howard |
| 2017/0333702 A1 | 11/2017 | Barner |
| 2017/0354825 A1 | 12/2017 | Dadashian et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0126175 A1 | 5/2018 | Seitz et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0060656 A1 | 2/2019 | Scott et al. |
| 2019/0083793 A1 | 3/2019 | Nageri |
| 2019/0083794 A1 | 3/2019 | Nageri |
| 2019/0103696 A1 | 4/2019 | Conger |
| 2019/0143125 A1 | 5/2019 | Van Funderburk et al. |
| 2019/0192861 A1 | 6/2019 | Lopez et al. |
| 2019/0217103 A1 | 7/2019 | Lopez |
| 2019/0290924 A1 | 9/2019 | Van Funderburk |
| 2019/0344085 A1 | 11/2019 | Stinauer et al. |
| 2020/0306540 A1 | 10/2020 | Aghassian |
| 2020/0346021 A1 | 11/2020 | Nageri et al. |
| 2021/0299454 A1 | 9/2021 | Nageri et al. |
| 2022/0273954 A1 | 9/2022 | Nageri et al. |
| 2023/0056675 A1 | 2/2023 | Lopez |

FOREIGN PATENT DOCUMENTS

| | | | |
|---|---|---|---|
| EP | 0832667 B1 | 2/2004 | |
| EP | 1181947 B1 | 1/2006 | |
| EP | 1625875 | 2/2006 | |
| EP | 2092952 A1 | 8/2009 | |
| EP | 3113837 B1 | 8/2021 | |
| WO | 1997032628 A1 | 9/1997 | |
| WO | 1999055411 A3 | 2/2000 | |
| WO | 2000038574 A1 | 7/2000 | |
| WO | 2001058520 A1 | 8/2001 | |
| WO | 2002068042 A1 | 9/2002 | |
| WO | 2004045707 A1 | 6/2004 | |
| WO | 2008018067 A2 | 2/2008 | |
| WO | 2008053789 A1 | 5/2008 | |
| WO | 2008100841 | 8/2008 | |
| WO | 2009025816 A1 | 2/2009 | |
| WO | 2009102536 A1 | 8/2009 | |
| WO | 2009/148939 | 12/2009 | |
| WO | WO-2013003237 A2 * | 1/2013 | ........... A61N 1/3718 |
| WO | 2013162775 A2 | 10/2013 | |
| WO | 2014018092 A1 | 1/2014 | |

OTHER PUBLICATIONS

"Advanced Ceramics, Nov. 3, 2016, Encyclopaedia Britannica Inc., Britannica Online Encyclopedia" (Year: 2016).

* cited by examiner

CONNECTORS FOR AN ELECTRICAL STIMULATION SYSTEM AND METHODS OF MAKING AND USING

CROSS-REFERENCE TO RELATED APPLICATIONS

This application claims the benefit under 35 U.S.C. § 119(e) of U.S. Provisional Patent Application Ser. No. 63/234,884, filed Aug. 19, 2021, which is incorporated herein by reference.

FIELD

The present disclosure is directed to the area of implantable electrical stimulation systems and methods of making and using the systems. The present disclosure is also directed to connectors for an electrical stimulation system, as well as the system and methods for making and using the connectors.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a connector that includes contact assemblies and non-conductive stack spacers separating the contact assemblies from each other, the contact assemblies and the stack spacers defining a connector lumen configured to receive a portion of an electrical stimulation lead, wherein the contact assemblies and stack spacers are brazed together forming a sealed connector stack that resists passage of fluid between the contact assemblies and stack spacers.

Another aspect is a connector that includes contact assemblies and non-conductive stack spacers separating the contact assemblies from each other, the contact assemblies and the stack spacers defining a connector lumen configured to receive a portion of an electrical stimulation lead, wherein the stack spacers are made of a non-conductive ceramic, crystalline, or glass material.

In at least some aspects, the stack spacers are ceramic. In at least some aspects, the connector further includes a braze material disposed between adjacent ones of the contact assemblies and the stack spacers. In at least some aspects, the connector further includes an end stop brazed to a proximal-most one of the contact assemblies. In at least some aspects, the connector further includes a flange brazed to a distal-most one of the contact assemblies.

In at least some aspects, the contact assembly includes an outer contact housing, an inner contact housing, and a connector contact. In at least some aspects, the outer contact housing is welded to the inner contact housing.

Yet another aspect is a control module that includes a sealed housing; an electronics subassembly disposed in the sealed housing; and any of the connectors described above coupled to the sealed housing, where the contact assemblies of the connector are electrically coupled to the electronics subassembly.

A further aspect is a lead extension that includes any of the connectors described.

Another aspect is a method of making a connector. The method includes forming a stack of contact assemblies and non-conductive stack spacers separating the contact assemblies from each other, wherein the contact assemblies and the stack spacers define a connector lumen configured to receive a portion of an electrical stimulation lead; and joining the contact assemblies and stack spacers to form a connector stack that resists passage of water between the contact assemblies and stack spacers.

In at least some aspects, the joining includes brazing the contact assemblies and stack spacers to form the connector stack. In at least some aspects, the forming and the joining includes flowing a glass material between the connector assemblies and hardening the glass material to form the stack spacers. In at least some aspects, the forming and the joining includes growing a crystalline material between the connector assemblies to form the stack spacers.

In at least some aspects, the method further includes attaching an end stop to a proximal-most one of the contact assemblies. In at least some aspects, the method further includes attaching a flange to a distal-most one of the contact assemblies. In at least some aspects, the method further includes coupling a retention block to the flange.

In at least some aspects, the contact assembly includes an outer contact housing, an inner contact housing, and a connector contact, wherein the forming and the joining includes forming a stack of the outer contact housings of the contact assemblies and the stack spacers separating the outer contact housings; joining the outer contact housings to the stack spacers; for each of the contact assemblies, inserting the inner contact housing and the connector contact into the outer contact housing; and physically attaching the outer contact housing to the inner contact housing. In at least some aspects, the method further includes inserting non-conductive, polymeric spacers between the connector contacts.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable electrical stimulation systems and methods of making and using the systems. The present disclosure is also directed to connectors for an electrical stimulation system, as well as the system and methods for making and using the connectors.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

The leads and electrical stimulation systems can be used for any suitable application including, but not limited to, deep brain stimulation, spinal cord stimulation, peripheral nerve stimulation, dorsal root ganglion stimulation, sacral nerve stimulation, or stimulation of other nerves, muscles, and tissues.

Figure 1:
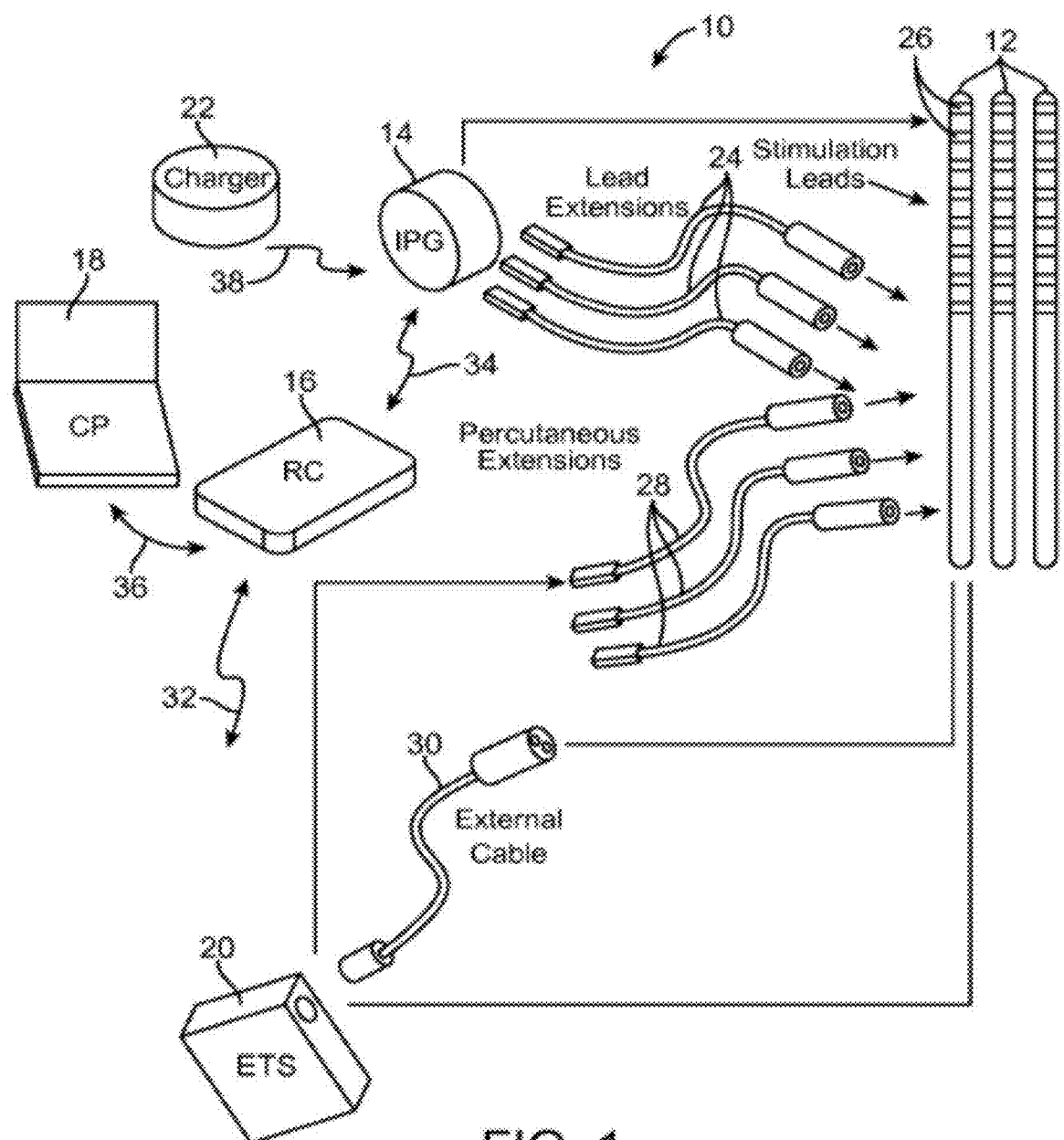
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In at least some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference in their entireties.

One or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads can include any suitable number of electrodes including, but not limited to, 4, 6, 8, 10, 12, 16, 20, 24, 30, 32, or more electrodes. The leads can include any suitable combination of ring electrodes, a distal-tip electrode, or one or more segmented electrodes. The term "elongated member" used herein includes leads (e.g., percutaneous, paddle, cuff, or the like), as well as intermediary devices (e.g., lead extensions, adaptors, splitters, or the like).

Figure 2:
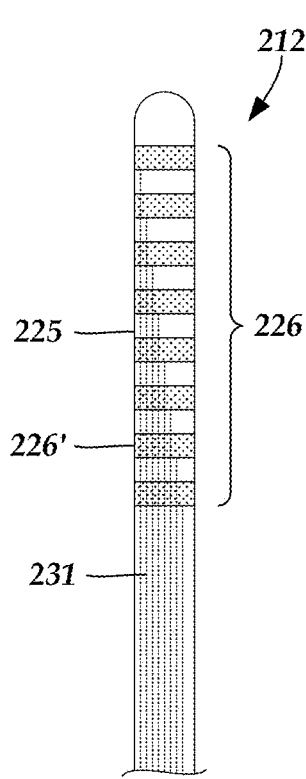
FIG. 2 is a schematic side view of one embodiment of an electrical stimulation lead.
Figure 2:
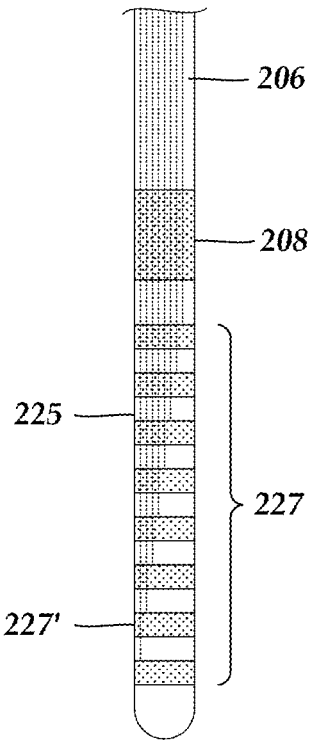

FIG. 2 shows, in schematic side view, one embodiment of a lead 212 suitable for implanting into a patient and providing electrical stimulation. In some embodiments, the lead 212 is coupled directly to a control module. In other embodiments, the lead 212 is coupled to the control module via one or more intermediary devices. In the illustrated embodiment, an array of electrodes 226, which includes electrode 226', is disposed along a distal portion of a lead body 206 lead and an array of lead terminals 227, which includes lead terminal 227', is disposed along a proximal portion of the lead body. Non-conductive spacers 225 separate the electrodes 226 and terminals 227 and may be part of the lead body 206 or separate elements added during construction of the lead 212. Lead conductors, such as lead conductor 231, extend along a longitudinal length of the lead and electrically couple the array of electrodes 226 to the array lead terminals 227.

Conductors can extend along the longitudinal length of the lead within one or more lumens defined in the lead. In other instances, the conductors may extend along the lead within the lead body itself. In at least some embodiments, the lead 212 includes a retention ring 208 disposed along the proximal portion of the body to facilitate coupling of the proximal portion of the lead to a connector. The connector may be disposed on or within a control module. Alternatively, the retention ring 208 can be used to facilitate coupling of the proximal portion of the lead to a connector of an intermediary device, such as a lead extension which, in turn, is coupled to a connector of a control module.

Figure 3:
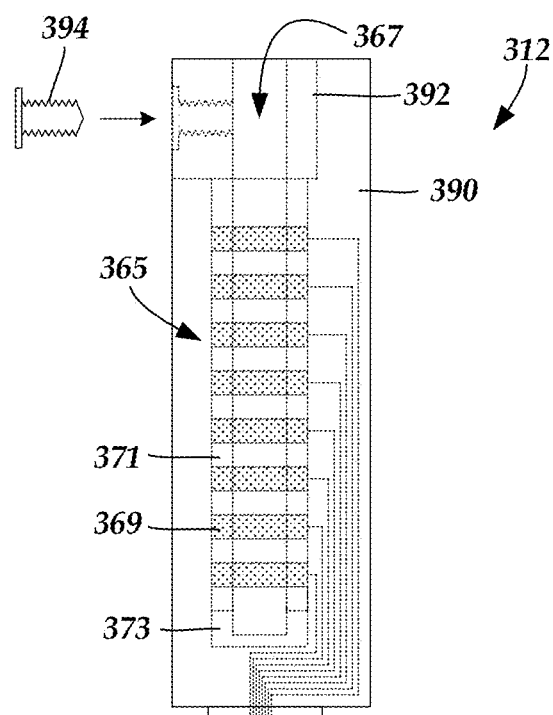
FIG. 3 is a schematic side view of one embodiment of a lead extension suitable for coupling with the electrical stimulation lead of FIG. 2.
Figure 3:
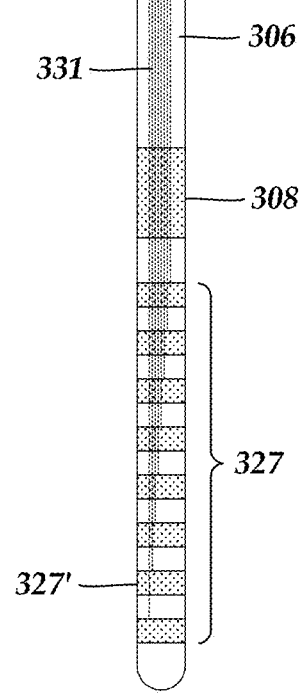

FIG. 3 shows, in schematic side view, one embodiment of a lead extension 312 suitable for implanting into a patient and coupling a lead, such as the lead 212, to a control module. The lead extension 312 includes a lead-extension body 306 having a distal portion and a proximal portion. A lead-extension connector 390 is disposed along the distal portion of the lead-extension body 306 and an array of lead-extension terminals 327, such as lead-extension terminal 327', are disposed along the proximal portion of the lead-extension body 306.

The lead-extension connector 390 contains a lead-extension connector stack 365 that defines a connector lumen 367 configured to receive the proximal portion of an elongated member (e.g., lead 212). The lead-extension connector stack 365 includes lead-extension connector contacts, such as lead-extension connector contact 369, arranged along the connector lumen 367 and configured to electrically couple with terminals of the elongated member (e.g., lead 212) when the proximal portion of the elongated member is received by the lead-extension connector 390. The connector contacts can be electrically isolated from one another by electrically-nonconductive spacers, such as spacer 371. The connector stack may also include an end stop 373 to promote alignment of the elongated-member terminals with the lead-extension connector contacts.

The lead-extension connector 390 further includes a retention assembly for facilitating retention of the proximal portion of the elongated member (e.g., lead 212) when the proximal portion of the elongated member is received by the lead-extension connector 390. In the illustrated embodiment, the retention assembly includes a lead-extension retention block 392. The lead-extension retention block 392 is positioned to align with the retention ring (208 in FIG. 2) of the elongated member when the elongated member is received by the lead-extension connector 390. In the illustrated embodiment, the retention assembly further includes a retaining member (e.g., a set screw, a pin, or the like) 394 for pressing the retention ring of the inserted elongated member against the retention block to retain inserted elongated member within the lead-extension connector 390.

Lead-extension conductors, such as lead-extension conductor 331, extend along a longitudinal length of the lead extension and electrically couple the lead-extension connector contacts to the array of lead-extension terminals 327. The lead-extension conductors can extend along the longitudinal length of the lead-extension body within one or more lumens defined in the lead extension. In other instances, the lead-extension conductors may extend along the lead extension within the lead-extension body itself. The lead extension 312 includes an retention ring 308 disposed along the proximal portion of the lead-extension body to facilitate coupling of the proximal portion of the lead extension to a connector, such as a control-module connector, another lead-extension connector, or the like.

Figure 4:
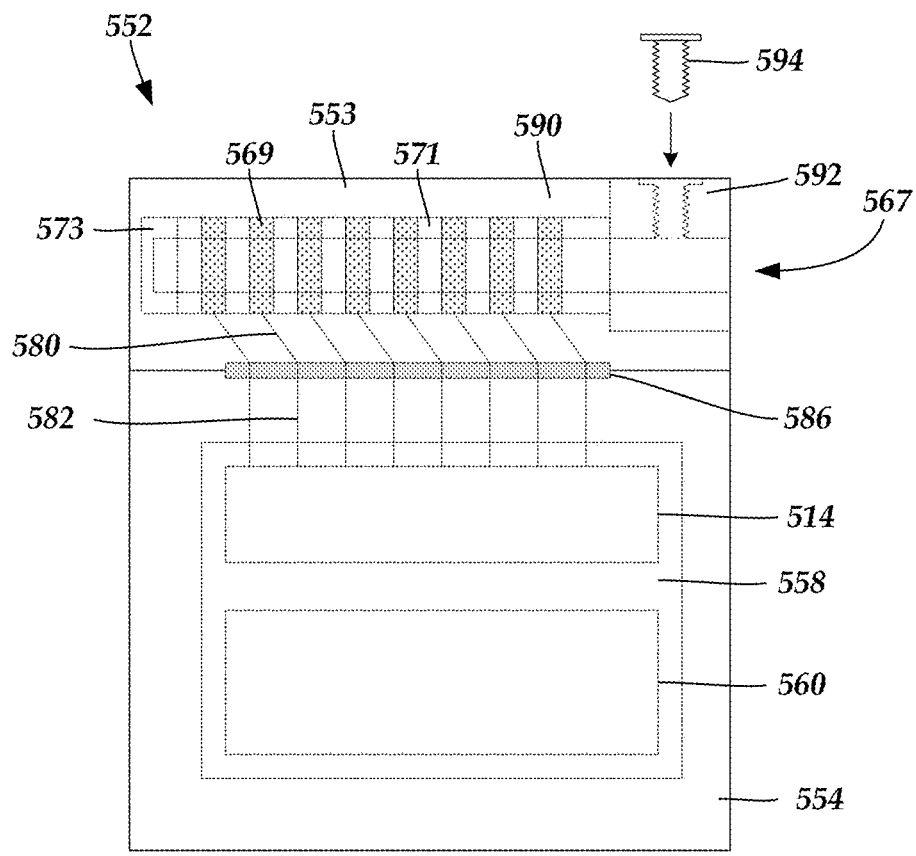
FIG. 4 is a schematic side view of one embodiment of a control module suitable for receiving either the lead of FIG. 2 or the lead extension of FIG. 3.

FIG. 4 shows, in schematic cross-sectional side view, a control module 552 suitable for coupling with an elongated member (e.g., the lead 212, the lead extension 312, or other intermediary device). The control module 552 includes a header 553 disposed along an outer surface of a sealed housing 554 that contains an electronic subassembly 558 with a pulse generator 514 and, optionally, a power supply 560.

A connector 590 is disposed in the header 553. The connector 590 is configured to receive an elongated device (e.g., the lead 212, the lead extension 312, or other intermediary device). The connector 590 defines a connector lumen 567 configured to receive the proximal portion of the elongated member. An array of connector contacts, such as connector contact 569, is arranged along the connector lumen 567 and configured to electrically couple with terminals of the elongated member when the proximal portion of the elongated member is received by the connector 590. The connector contacts can be electrically isolated from one another by electrically-nonconductive spacers, such as spacer 571. The connector stack may also include an end stop 573 to promote alignment of the elongated-member terminals with the connector contacts.

Wires or contacts, such as wire 582, are electrically coupled to the electrical subassembly 558 and extend within the sealed housing 554 to a feedthrough interface 586 disposed along an interface between the header 553 and the sealed housing 554. The connector contacts are electrically coupled to interconnect conductors, such as wire 580, that extend along the header 553 and electrically couple the connector contacts to the wires 582 (and possibly feedthrough pins) at the feedthrough interface 586. In some embodiments, the header 553 is positioned over the feedthrough interface 586.

The connector 590, optionally, includes a retention assembly for facilitating retention of the proximal portion of the elongated member when the proximal portion of the elongated member is received by the control module 552. In the illustrated embodiment, the retention assembly includes a retention block 592. The retention block 592 is positioned to align with a retention sleeve of the elongated member when the elongated member is received by the connector 590. In the illustrated embodiment, the retention assembly further includes a retaining member (e.g., a set screw, a pin, or the like) 594 for pressing the retention sleeve of the inserted elongated member against the retention block to retain inserted elongated member within the connector 590.

Figure 5A:
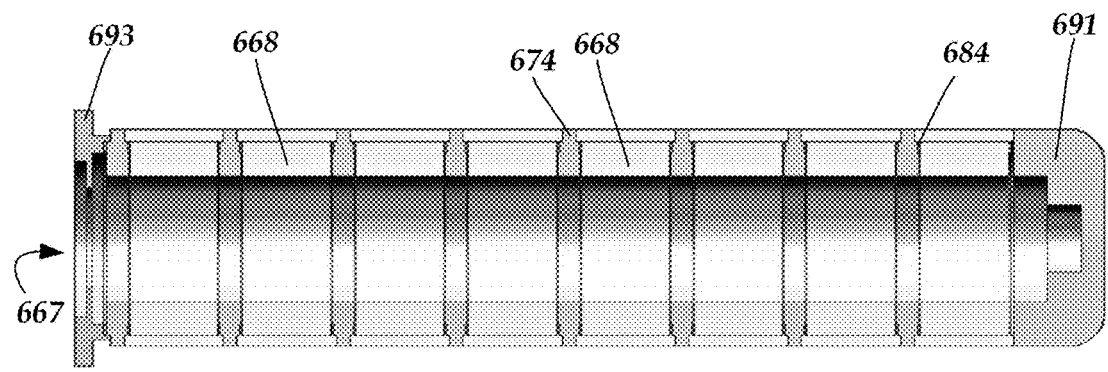
FIG. 5A is a schematic cross-sectional view of one embodiment of a stack, including multiple contacts, for a connector assembly.
Figures 5B, 5C, 5D:
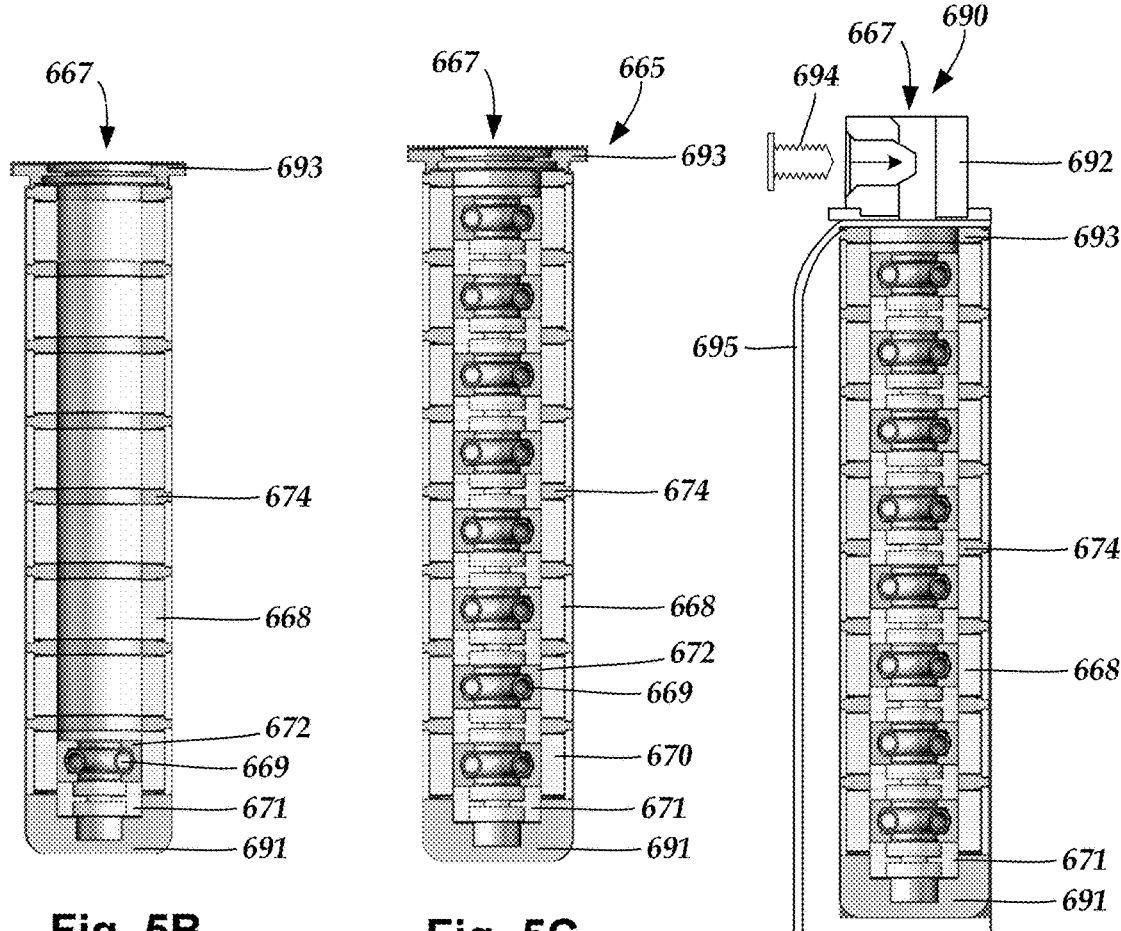
FIG. 5B is a schematic cross-sectional view of the stack of FIG. 5A with a single contact inserted into the stack.
FIG. 5C is a schematic cross-sectional view of the stack of FIG. 5A with a full set of contacts inserted into the stack.
FIG. 5D is a schematic cross-sectional view of one embodiment of connector assembly with the stack and set of contacts of FIG. 5C.

FIGS. 5A to 5D illustrate one embodiment of the manufacture of a connector 690 which can be a connector of a lead extension 312, such as lead extension connector 390, or a connector of a control module 552, such as connector 590, or any other suitable connector for receiving terminals 227, 327 of a lead 212 or lead extension 312 or the like. The connector 690 includes a connector stack 665 that defines a connector lumen 667 and includes contact assemblies 670, stack spacers 674, non-conductive spacers 671, an end stop 691, and an optional flange 693 disposed along the connector lumen 667, as illustrated in FIG. 5C.

In at least some embodiments, the connector 690 can be a hermetic connector. There is interest in hermetic connectors. A hermetic connector prevents or substantially resists the flow of fluid, such as water or bodily fluids, from the connector lumen 667 through, or between, the contact assemblies 670 and stack spacers 674 to enter, for example, the header 553 (FIG. 4) (or sealed housing 554 (FIG. 4) when the connector extends into the sealed housing instead of the header 553—see, FIG. 6.) In at least some embodiments, a hermetic connector can be disposed in the sealed housing 554 to eliminate a feedthrough interface 586 and separate header 553, as illustrated, for example, in FIG. 6.

In at least some embodiments, the stack spacers 674 can be made of any suitable non-conductive ceramic, crystalline, or glass material including, but not limited to, aluminum oxide (including, but not limited to, alumina or crystalline aluminum oxide such as corundum, ruby, or sapphire), glass, or the like or any combination thereof. The stack spacers 674 can be formed by any suitable method including, but not limited to, molding (for example, by molding a ceramic material or by melting glass and pouring into a mold), crystal growth, or the like or any combination thereof. In at least some embodiments, the end stop 691 is also made of the same material as the stack spacers 674.

In at least some embodiments, the contact assembly 670 includes a connector contact 669, an inner contact housing 672, and an outer contact housing 668, as illustrated in FIG. 5B. The inner contact housing 672 holds the contact 669 in position along the connector lumen 667 in order to make contact with terminals 227, 327 of a lead 212 or lead extension 312. The outer contact housing 668 can be separate element to facilitate construction of the connector stack 665 as described below. In at least some embodiments, the inner contact housing 672 and outer contact housing 668 are a single element (for example, a single contact housing) or are both absent from the contact assembly 670.

In at least some embodiments, the outer contact housings 668 (or the contact assemblies 670) and stack spacers 674 are arranged in an alternating pattern. The outer contact housings 668 (or the contact assemblies 670), stack spacers 674, end stop 691, and, optionally, the flange 693 are joined together, as illustrated in FIG. 5A. In at least some embodiments, this joining forms a sealed connector stack that resists the passage of water and bodily fluids (and, at least in some embodiments, other fluids, such as helium or other gases) between the contact housings 668 (or the contact assemblies 670) and stack spacers 674.

In at least some embodiments, the outer contact housings 668 (or the contact assemblies 670), stack spacers 674, end stop 691, and, optionally, the flange 693 are joined together by brazing. In at least some embodiments, the brazing of the outer contact housings 668 (or contact assemblies 670), stack spacers 674, end stop 691, and, optionally, the flange 693 forms a hermetic structure that prevents or resists passage of fluid, such as water, bodily fluids, or the like through the hermetic structure. In at least some embodiments, the hermetic structure prevents or resists passage of helium or other gas through the hermetic structure. In at least some embodiments, to facilitate brazing, the connector stack 665 includes a braze material 694 selected to braze the outer contact housings 668 (or contact assemblies 670) to the stack spacers 674. For example, the braze material 694 can be gold, or the like or any combination thereof. In at least some embodiments, the braze material 694 is selected based on the materials of the outer contact housings 668 and stack spacers 674.

Other methods of joining the outer contact housings 668 (or the contact assemblies 670) and stack spacers 674 (and optionally one or both of the end stop 691 and the flange 693). For example, one method includes flowing or otherwise disposing a glass material between the outer contact housings (or the contact assemblies 670) and solidifying or hardening the glass material to form the stack spacers 674. Another method includes growing a crystalline material between the outer contact housings (or the contact assemblies 670) to form the stack spacers 674. Yet other methods forming an alternating stack of the outer contact housings 668 (or the contact assemblies 670) and stack spacers 674 and applying pressure on the stack to join the outer contact housings 668 (or the contact assemblies 670) and stack spacers 674. Any other suitable method for joining or forming the stack of outer contact housings 668 (or the contact assemblies 670) and stack spacers 674 can be used.

In at least some embodiments, as illustrated in FIGS. 5B and 5C, subsequently the non-conductive spacers (or seals) 671 and connector contacts 669 (within the inner contact housing 672) are alternatively inserted into the connector lumen 667. The non-conductive spacers 671 separate and electrically isolate the connector contacts 669 from each other.

In at least some embodiments, each of the contact housings 672 of each of the connector contacts 669 is electrically coupled to a corresponding one of the outer contact housing 668 (for example, physically coupled by seam or spot welding using a laser or the like, soldering, or otherwise forming a physical attachment of the inner contact housing 672 or connector contact 669 to the outer contact housing 668) to form the contact assembly 670 after the connector contact 669 is placed. Other methods for electrically coupling the connector contact 669 (within the inner contact housing 672) to the outer contact housing 668 can be used including, but not limited to, passive coupling through contact between the inner contact housing 672 and the outer contact housing 668.

In an alternative method of manufacture, instead of just the outer contact housing 668, the entire contact assembly 670 can be stacked and brazed with the stack spacers 674. Then, non-conductive spacers 671 can be formed between the connector contacts 669 by injecting a non-conductive material such as a polymeric material (for example, silicone) or a polymer precursor into the connector lumen 667 and then cooling, crosslinking, or otherwise modifying the non-conductive material to form the spacers 671. In at least some embodiments, a mandrel can be inserted into the connector lumen 667 after injecting the non-conductive material, and, optionally, prior to forming the spacers 671, to facilitate clearing the connector lumen of the non-conductive material.

In FIG. 5D, the connector stack 665 is welded into a case 695 and the retention block 692 (with fastener 694) is coupled to the flange 693 or connector stack 665 to produce the connector 690. In at least some embodiments, the connector 690 provides a hermetic seal against the passage of fluid, such as water, bodily fluids, helium or other gas, or the like.

Figure 6:
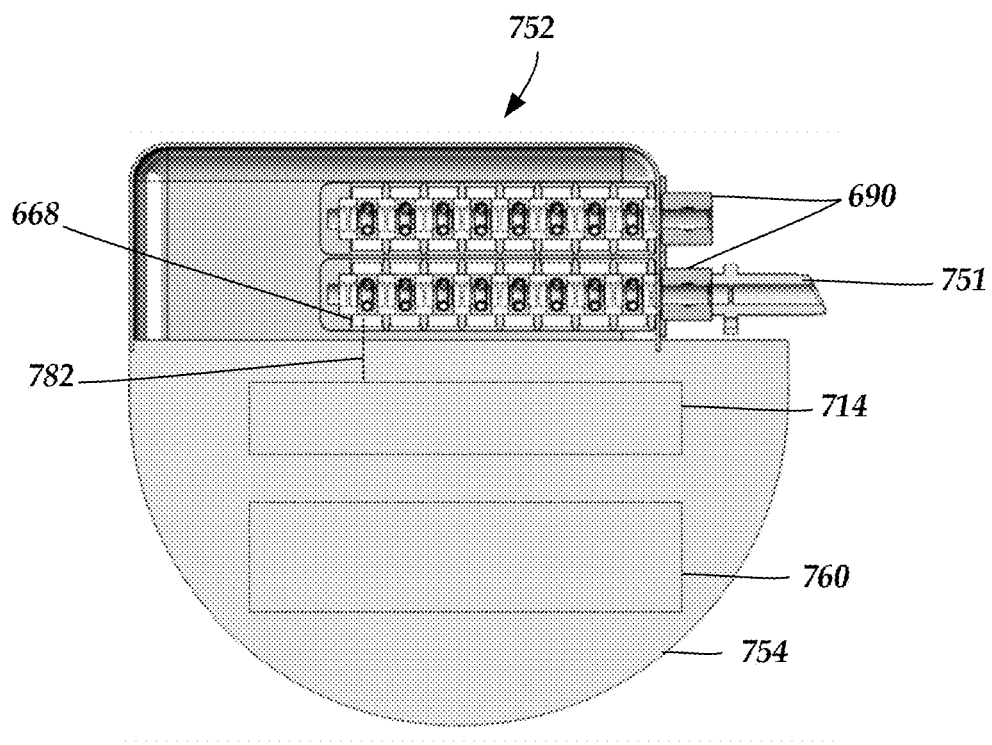
FIG. 6 is a schematic cross-sectional view of one embodiment of control module with two of the connector assemblies of FIG. 5D.

In at least some embodiments, as illustrated in FIG. 6, a hermetic connector 690 can be part of a control module 752 that does not include a header 553 (FIG. 4) or feedthrough interface 586 (FIG. 4). (The header 553 and feedthrough interface 586 are typically provided to couple non-hermetic connectors 590 to a hermetically sealed housing 554.) The control module 752 can include a sealed housing 754 with one or more of the hermitic connectors 690 extending into the sealed housing. The control module 752 can include a pulse generator 714 and optional power source 760. The pulse generator can be coupled to the contacts 669 by wires 782.

In at least some embodiments, a strain relief component 751 can extend from the connector 690, as illustrated in FIG. 6. For example, the strain relief component 751 can be made of silicone or other flexible material. In at least some embodiments, for a control module 752 with multiple connectors 690, an individual strain relief component 751 can extend from each connector 690. These strain relief components 751 can be separate from each other or can be connected to one another (or to a subset of each other).

Figure 7:
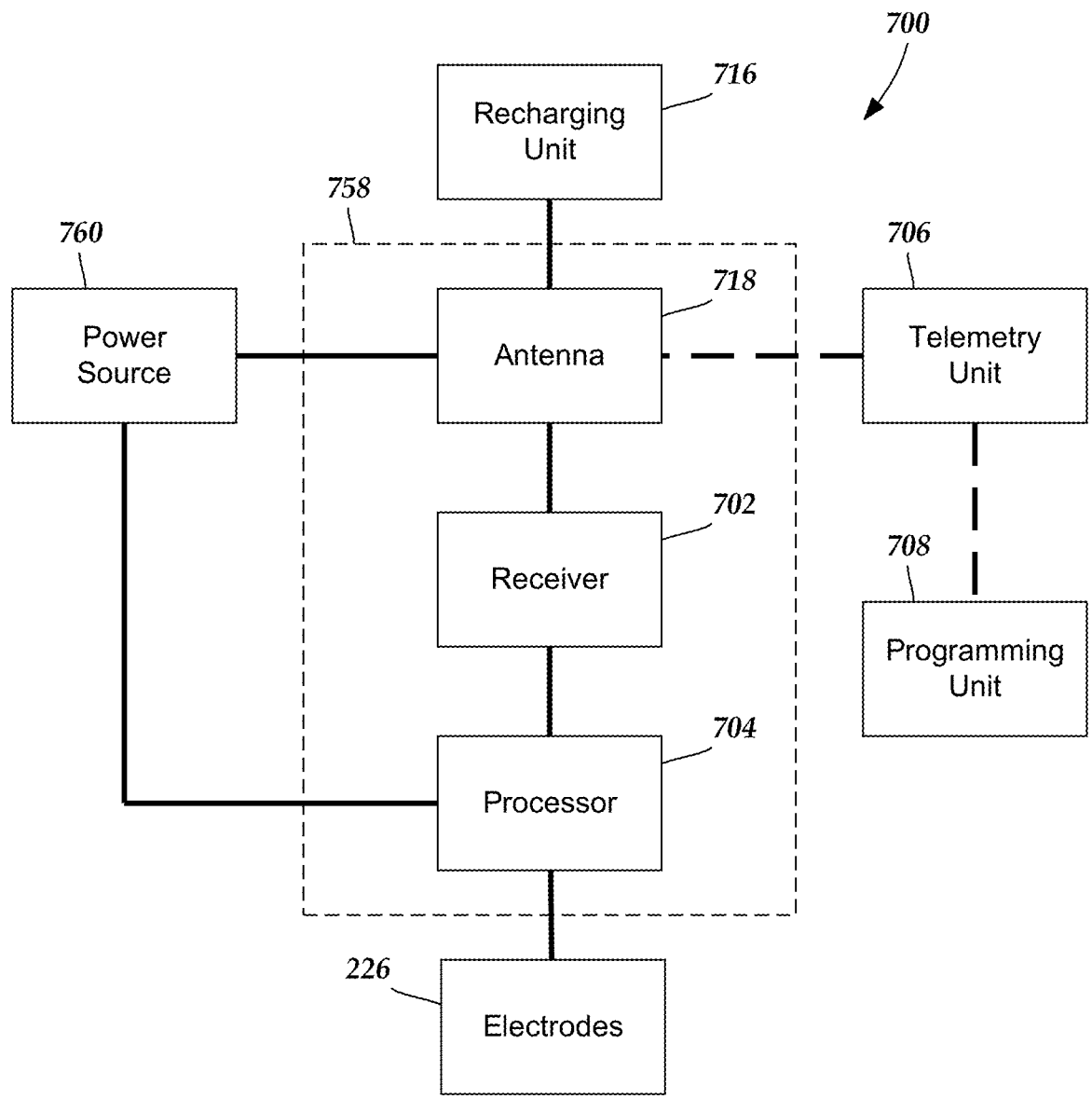
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 758 disposed within a control module. The electronic subassembly 758 may include one or more components of the IPG. It will be understood that the electrical stimulation system can include more, fewer, or different components and can have a variety of different configurations including those configurations disclosed in the stimulator references cited herein.

Some of the components (for example, a power source 760, an antenna 718, a receiver 702, and a processor 704) of the electrical stimulation system can be positioned on one or more circuit boards or similar carriers within a sealed housing of an implantable pulse generator (see e.g., 14 in FIG. 1), if desired. Any power source 760 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 760 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above. The electronic subassembly 758 and, optionally, the power source 760 can be disposed within a control module (e.g., the IPG 14 or the ETS 20 of FIG. 1).

In one embodiment, electrical stimulation signals are emitted by the electrodes (e.g., 26 in FIG. 1) to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A connector, comprising:
   a plurality of contact assemblies, wherein each of the contact assemblies comprises an outer contact housing, a separate inner contact housing attached to the outer contact housing, and a connector contact; and
   a plurality of non-conductive stack spacers separating the contact assemblies from each other, the contact assemblies and the stack spacers forming a connector stack defining a connector lumen configured to receive a portion of an electrical stimulation lead, wherein the contact assemblies and stack spacers are brazed together forming a sealed connector stack that resists passage of fluid between the contact assemblies and stack spacers, wherein, for each of the contact assemblies, the outer contact housing has a longer width, along the connector lumen, than the inner contact housing.

2. The connector of claim 1, wherein the stack spacers are ceramic.

3. The connector of claim 1, further comprising a braze material disposed between adjacent ones of the contact assemblies and the stack spacers.

4. The connector of claim 1, further comprising an end stop brazed to a proximal-most one of the contact assemblies.

5. The connector of claim 1, further comprising a flange brazed to a distal-most one of the contact assemblies.

6. The connector of claim 1, wherein the outer contact housing is welded to the inner contact housing.

7. A control module, comprising:
   a sealed housing;
   an electronics subassembly disposed in the sealed housing; and
   the connector of claim 1 coupled to the sealed housing, wherein the contact assemblies of the connector are electrically coupled to the electronics subassembly.

8. A method of making the connector of claim 1, the method comprising:
   forming the connector stack of the plurality of contact assemblies and the plurality of stack spacers separating the contact assemblies from each other; and
   joining the contact assemblies and stack spacers to resist passage of water between the contact assemblies and stack spacers.

9. The method of claim 8, wherein the joining comprises brazing the contact assemblies and stack spacers to form the connector stack.

10. The method of claim 8, wherein the forming and the joining comprises flowing a glass material between the contact assemblies and hardening the glass material to form the stack spacers.

11. The method of claim 8, wherein the forming and the joining comprises growing a crystalline material between the contact assemblies to form the stack spacers.

12. The method of claim 8, further comprising attaching an end stop to a proximal-most one of the contact assemblies.

13. The method of claim 8, further comprising attaching a flange to a distal-most one of the contact assemblies.

14. The method of claim 13, further comprising coupling a retention block to the flange.

15. The method of claim 8, wherein the contact assembly comprises an outer contact housing, an inner contact housing, and a connector contact, wherein the forming and the joining comprises
   forming a stack of the outer contact housings of the contact assemblies and the stack spacers separating the outer contact housings;
   joining the outer contact housings to the stack spacers;
   for each of the contact assemblies, inserting the inner contact housing and the connector contact into the outer contact housing; and
   physically attaching the outer contact housing to the inner contact housing.

16. The method of claim 15, further comprising inserting non-conductive, polymeric spacers between the connector contacts.

17. The connector of claim 1, wherein, with respect to the contact assemblies, the stack spacers only engage the outer contact housing.

18. The connector of claim 1, wherein each of the plurality of stack spacers separating two of the contact assemblies is directly brazed to the outer contact housings of both of the two of the contact assemblies.

19. The connector of claim 1, further comprising a plurality of non-conductive, polymeric spacers disposed radially inward of the stack spacers and separating the contact assemblies from each other.

20. The connector of claim 19, wherein each of the plurality of non-conductive, polymeric spacers separating two of the contact assemblies directly engages the inner contact housings of both of the two of the contact assemblies.

* * * * *